United States Patent [19]
Darras et al.

[11] Patent Number: 5,336,555
[45] Date of Patent: Aug. 9, 1994

[54] SURGICAL GLOVE COMPRISING CARBON FIBER WHISKERS

[76] Inventors: Robert L. Darras, 2219 Mount Shasta Dr., San Pedro, Calif. 90732; Tau-chao Fan, 30571 Rue De La Pierre, Rancho Palos Verdes, Calif. 90274

[21] Appl. No.: 698,550

[22] Filed: May 10, 1991

[51] Int. Cl.$^5$ .................. A41D 19/00; D03D 15/00; B32B 5/12
[52] U.S. Cl. .................. 428/247; 428/245; 428/253; 428/254; 428/282; 428/284; 428/286; 428/288; 428/290; 428/408; 428/902; 428/911; 2/159
[58] Field of Search .............. 2/161, 167, 159, 161 R; 428/911, 408, 247, 248, 246, 245, 253, 254, 282, 284, 286, 288, 290, 902

[56] References Cited

U.S. PATENT DOCUMENTS

| | | | |
|---|---|---|---|
| 3,184,756 | 5/1965 | DeLuca, Jr. | 2/167 |
| 3,773,898 | 5/1975 | Byrnes, Sr. | 2/167 |
| 3,945,049 | 3/1976 | Barlow . | |
| 4,004,295 | 1/1977 | Byrnes, Sr. | 2/161 R |
| 4,115,873 | 9/1978 | Stansbury | 2/163 |
| 4,189,787 | 2/1980 | Stansbury | 2/163 |
| 4,218,778 | 8/1980 | Stansbury | 2/163 |
| 4,218,779 | 8/1980 | Hart et al. . | |
| 4,371,988 | 2/1983 | Berend | 2/167 |
| 4,454,611 | 6/1984 | Tschirch et al. | 2/161 R |
| 4,470,251 | 9/1984 | Bettcher | 57/230 |
| 4,507,804 | 4/1985 | Consigny | 2/21 |
| 4,513,047 | 4/1985 | Leach et al. | 264/103 |
| 4,526,828 | 7/1985 | Fogt et al. | 428/911 |
| 4,540,624 | 9/1985 | Cannady, Jr. | 428/282 |
| 4,578,826 | 4/1986 | Adiletta | 2/167 |
| 4,613,535 | 9/1986 | Harpell et al. | 428/113 |
| 4,729,860 | 3/1988 | Leach | 428/175 |
| 4,732,803 | 3/1988 | Smith, Jr. | 428/212 |
| 4,737,402 | 4/1988 | Harpell et al. | 428/252 |
| 4,778,717 | 10/1988 | Fitchmun | 428/246 |
| 4,779,290 | 10/1988 | Welch et al. | 2/161 R |
| 4,786,541 | 11/1988 | Nishimura et al. | 428/113 |
| 4,833,733 | 5/1989 | Welch et al. | 2/169 |
| 4,864,660 | 9/1989 | Sawyer | 2/161 A |
| 4,868,038 | 9/1989 | McCullough, Jr. et al. | 428/222 |
| 4,869,947 | 9/1989 | Kirayogla | 428/198 |
| 4,906,506 | 3/1990 | Nishimura et al. | 428/102 |
| 4,912,781 | 4/1990 | Robins et al. | 2/167 |

OTHER PUBLICATIONS

T. C. Fan and Janet Knapp, "Properties Of Composites", Jul. 1987.

*Primary Examiner*—Patrick J. Ryan
*Assistant Examiner*—Richard C. Weisberger
*Attorney, Agent, or Firm*—Spensley Horn Jubas & Lubitz

[57] ABSTRACT

A slash resistant composite material and surgical glove made of such material. The composite material comprises a polymeric matrix having embedded therein hard material whiskers which are oriented randomly in the matrix. The whiskers consist of a material selected from the group consisting of silicon carbide, carbon and mixtures thereof. The diameter of the whiskers ranges from 0.00015 to 0.0005 inches and the length of the whiskers ranges from 0.0625 to 0.125 inches.

4 Claims, 1 Drawing Sheet

SURGICAL GLOVE COMPRISING CARBON FIBER WHISKERS

FIELD OF THE INVENTION

The instant invention relates to a slash resistant material particularly well suited for use as surgical gloves.

BACKGROUND OF THE INVENTION

There is a need in surgical situations for a slash-resistant surgical glove. Such a glove can contribute to the prevention of transmission of blood-borne infections, such as AIDS and hepatitis during surgery. For example, it is common during surgery for a surgeon to be nicked by a scalpel. In this manner, the scalpel can transmit blood-borne infections from the patient to the surgeon.

Some surgical gloves are made from a thin layer of latex. Examples of latex rubber gloves for medical use are disclosed in U.S. Pat. No. 4,115,873 to Stansbury, issued Sep. 26, 1978; U.S. Pat. No. 4,189,787 to Stansbury, issued Feb. 26, 1980; and U.S. Pat. No. 4,218,778 to Stansbury, issued Aug. 26, 1980. This type of latex glove provides excellent tactility for the surgeon yet is easily susceptible to scalpel cuts.

Cut-resistant gloves known in the prior art include various means incorporated therein for guarding against injury by a knife or a scalpel. For example, U.S. Pat. No. 4,507,804 to Consigny, issued Apr. 2, 1985, discloses a finger guard for protection against injury by a knife. The finger guard consists of a multiplicity of spaced-apart interconnected metallic lamellae. U.S. Pat. No. 3,184,756 to De Luca, Jr., issued May 25, 1965, provides a protective glove incorporating armor pieces in the finger portions. U.S. Pat. No. 4,470,251 to Bettcher, issued Sep. 11, 1984, discloses a knitted safety glove made of yarn having a core of two longitudinal strands of annealed stainless steel wire and one strand of high strength aramid fiber surrounded by an aramid fiber wrapped thereabout in one direction and a layer of nylon wrapped upon the first layer and in the opposite direction.

U.S. Pat. No. 4,540,624 to Cannady, issued Sep. 10, 1985, discloses a static-dissipating laminate. The laminate includes long and thin carbon fibers uniformly distributed throughout a fibrous print layer and a fibrous core layer. The carbon fibers have lengths from about 0.20 inch to about 0.75 inch, and diameters ranging from about 0.3 mil to about 3.0 mils. The carbon fibers are present in an amount from 1 wt. % to about 15 wt. %.

Also known are surgical gloves comprised of KEVLAR ® [poly(phenylenediamine terephthalate), manufactured by E. I. DuPont], which are approximately 3 mm thick. Such KEVLAR ® surgical gloves have a very low sheer. However, KEVLAR ® by itself does not resist cuts or slashing; only by using multiple layers of KEVLAR ® is some resistance facilitated.

These prior art gloves and finger guards are inapplicable to the situation confronted by the surgeon wherein it is first necessary to have sufficient tactility to perform delicate surgical maneuvers while it is desirable to have protection against scalpel cuts. The aforementioned prior art patents disclose either gloves which provide tactility but no cut protection or provide knife cut protection with the sacrifice of the necessary tactility.

There exists various methods for manufacturing multi-layered gloves having protective layers. U.S. Pat. No. 3,945,049 to Barlow, issued Mar. 23, 1976 discloses a process for the manufacture of gloves including the steps of precoating the fabric, curing the precoat, and then welding two pieces together along a weld zone thereby creating a seam. U.S. Pat. No. 4,371,988 to Berend, issued Feb. 8, 1983, discloses a method for making a protective two-layer coating on a glove including the steps of soaking a mold covered with a lining in a first mixture of a resin and pre-gelling the first protective layer. The lining provided with the first layer is then subjected to a partial soaking in a second mixture of resin and the layers are gelled.

U.S. Pat. No. 4,578,826 to Adiletta, issued Apr. 1, 1986, discloses a process for manufacturing protective gloves including the steps of drawing a vacuum to the interior of a fabric shell to cause a binding agent and fibers from a slurry to be deposited on the outer surface of the shell. A composite structure is cured to set the matrix in the desired shape.

U.S. Pat. No. 4,218,779 to Hart et al, issued Aug. 16, 1980, discloses a method of manufacturing a chemical-resistant glove including several steps of dipping treated substrates in a bath containing a latex dispersion. Latex-dipped gloves are air-or oven-dried to produce a rubber coated form.

Other cut-resistant surgical gloves and methods for making such surgical gloves are discussed in U.S. Pat. No. 4,833,733 to Welch, issued May 30, 1989, and U.S. Pat. No. 4,779,290 to Welch, issued Oct. 25, 1988.

SUMMARY OF THE INVENTION

The present invention is directed to a slash resistant material which is particularly useful in forming surgical gloves. The present invention provides a surgical glove allowing the surgeon to have the tactile response necessary for delicate surgical maneuvers but also provides a cut resistant surface. The present invention further provides a method for manufacturing the glove.

In general the present invention comprises a polymeric matrix layer having embedded therein hard material whiskers, and/or particulates.

In one embodiment of the invention, the composite material comprises a polymeric matrix layer having embedded therein whiskers selected from the group consisting of carbon whiskers silicon carbide whiskers, and mixtures thereof, wherein the diameter of the whiskers ranges from 0.00015 to 0.0005 inches and the length of the whiskers ranges from 0.0625 to 0.125 inches.

In another embodiment of the invention, the composite material comprises a polymeric matrix layer having embedded therein hard material whiskers, wherein the whiskers are oriented randomly in the matrix.

In yet another embodiment, the present invention is directed to a surgical hand glove comprising a polymeric layer having embedded therein hard material whiskers, wherein the volumetric ratio the whiskers to the polymer matrix ranges from 27% to 30%.

BRIEF DESCRIPTION OF THE DRAWINGS

Other advantages of the present invention will be readily appreciated as the same become better understood by reference to the following detailed description when considered in connection with the accompanying drawings wherein.

DETAILED DESCRIPTION OF THE PREFERRED EMBODIMENTS

Figure 1:
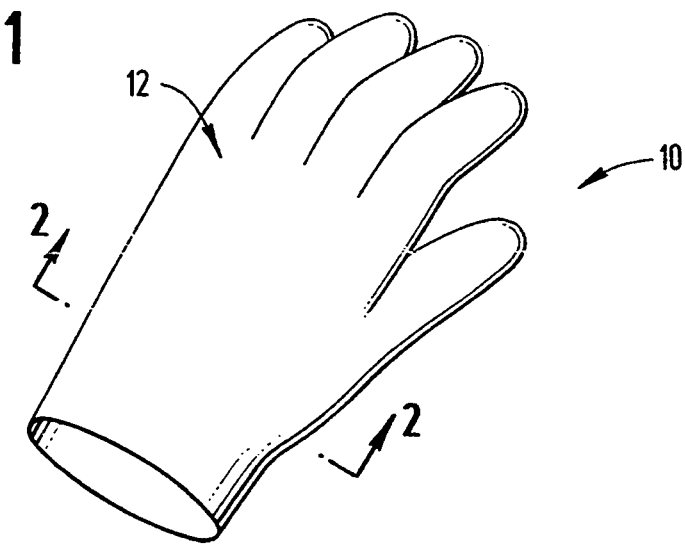
FIG. 1 is a perspective view of a surgical glove constructed in accordance with the present invention.

A surgical glove constructed in accordance with the present invention is generally shown at 10 in FIG. 1 of the drawings.

The glove 10 includes a ventral side (not shown) and a dorsal side generally indicated at 12, preferably integrally connected together. By being integral there is no seam between the ventral side and the dorsal side 12.

Figure 2:
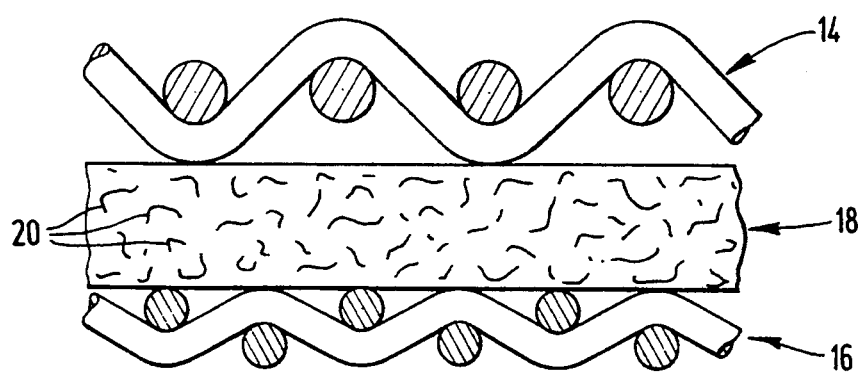
FIG. 2 is a blown-up fragmentary cross sectional view taken substantially along lines 2—2 of FIG. 1 and showing only the dorsal side of the glove.

As shown in FIG. 2, the glove 10 preferably includes two layers 14 and 16 comprised of a fibrous material, preferably a woven material, having sandwiched therebetween a polymeric matrix layer 18 with randomly oriented whiskers 20. Optimally, the two outer polymeric layers 14 and 16 have different weaves, as shown.

The layers 14 and 16 preferably are comprised of a stretchable interwoven material which can be made from a synthetic fiber. Examples of fibers which are cut-or slash-resistant are nylon and the aramid fibers. Aramid fibers are particularly suited for the present invention as they are heat resistant and therefore can be easily sterilized. They are dimensionally stable, and have ultra-high strength and high modulus. A particular aramid fiber well suited for the invention is the ultra-high strength, high-modules KEVLAR ® [poly(-phenylenediamine terephalamide)], manufactured by E. I. DuPont.

Although the KEVLAR ® polymeric matrix is preferred, other compatible non-metallic matrices are also within the scope of the present invention, such as latex. Other suitable polymeric matrices include those sold under the trademark "DACRON ®" or a combination of any of the polymers discussed above. It goes without saying that it is important that there be coherence between the polymeric matrix and the whiskers.

One method of making a surgical glove in accordance with the present invention includes providing a mold shell or mandrel having a handle portion and a hand form portion. The hand form portion is dipped into a container of the polymer mixture having whiskers stirred therein, the liquid being curable to the stretchable air-and water-permeable material discussed above.

Initially, preferably, a first layer of the polymeric matrix is disposed on the mold shell and thereafter at least partially cured by air drying or subjection to heat. Thereafter, a second layer consisting of the polymeric matrix having carbon whiskers stirred therein is applied to the first layer and allowed to at least partially cure. Thereafter, one or more additional layers may be applied and the glove appropriately cured.

As another example, the polymeric matrix having whiskers embedded therein can be nylon with carbon whiskers, and this layer can be sandwiched between a layer of KEVLAR ® and another layer of KEVLAR ® having a different weave than the first layer.

The whiskers found in the composite material of the present invention are preferably randomly oriented. They need not necessarily interconnect with each other, although they can be somewhat interconnected and can also be lined up or otherwise oriented.

In general, the whiskers can be selected from the group consisting of carbon whiskers silicon carbide whiskers, or mixtures thereof, with carbon whiskers preferred. For surgical gloves the whiskers can range in diameter from 0.00015 to 0.0005 inches, preferably 0.0002 to 0.0005 inches, and optimally 0.0003 to 0.0004 inches. For surgical gloves, the length of the whiskers can range from 0.0625 to 0.125 inches,,preferably 0.0625 to 0.125 inches, and optimally, 0.085 to 0.110 inches.

For purposes of surgical gloves, as discussed below, if carbon whiskers are chosen for whiskers, and the length of the whiskers is less than 0.0625 inches, silicon carbide particles can be added to the composite to achieve the desired slash resistancy without decreasing tactility.

Depending on the use of the composite material, one or more layers of the composite material (whiskers embedded in polymer matrix) can be used either alone, or interspersed with polymeric matrix layers. In addition, a variety of different polymeric matrix layers can be used. For example, as discussed above, for surgical gloves, one can use one layer of KEVLAR ® having embedded therein the whiskers, with such composite layers sandwiched in laminate fashion between two other layers of KEVLAR ® having different weaves.

For surgical gloves having KEVLAR ® as the matrix and carbon whiskers within the preferred range above, and a glove thickness of 3 mil to 5 mil, it is important that the volumetric ratio of whiskers to the polymer matrix be within a certain range, generally from 27% to 30%, preferably, from 27.5 to 29.5, with about 28.5% being optimal. As the percentage increases, the glove has reduced elasticity and becomes more stiff. As the percentage decreases, the slash resistancy or strength decreases.

Preferably, for surgical gloves, the thickness of the glove is at least 3 mil but less than 5 mil. As the number and thickness of composite layers increase, the slash resistance increases and the tactility decreases.

Thus optimally, a surgical glove of the present invention can be formed having the three layer sandwich construction described above the entire sandwich being about 3–5 mils thick, with the volumetric ratio of carbon to KEVLAR ® ratio of the laminate layer being about 28.5%.

In some instances, it may be desirable to have a volumetric ratio less than 27%, however, multiple layers should be then used to achieve the slash resistancy. For example, at a volumetric ratio of 24% with two composite layers totaling 10 mils thick, the desired slash resistance is present; however, the tactile sense is decreased.

If one does not use the composite material for surgical gloves and thus does not need the flexibility, one can increase the volumetric ratio above 30%.

In order to make the composition of the present invention the selected polymer, for example, KEVLAR ® can be heated under pressure until it is liquid. The whiskers can be added by sprinkling and the mixture stirred. A glove mandrel can be dipped in the liquid and thereafter cooled.

As is known in the art, it is important that the matrix be cured properly at an appropriate cooling rate so that the whiskers are embedded in the matrix and are not loose. It is also important to control the humidity in the manufacturing room to achieve this result as is also known in the art.

The cooling rate for proper curing to minimize thermal strain and thereby cracks can be achieved by using whisker and matrix materials having similar thermal conductivity, preferably within 20% of each other.

From a temperature constraint, if the composite matrix is used in environments where the temperature is less than 300° C., carbon whiskers are useful in either KEVLAR ®, latex or epoxy matrices. Above 300° C. a polyamide matrix maybe more preferable.

A 5 mil thick triple layer surgical glove prepared according to the above directions using latex with carbon whiskers or KEVLAR ® with carbon whiskers and an optimum volumetric ratio of about 28.5% has a density of about 0.62 pounds per cubic inch, a fracture strength of about 16,000 psi, and elastic modulous of about 1,250,000 psi, a sheer strength of about 19,000 psi and a tensile strength of about 50,000 psi.

The invention has been described in an illustrative manner, and is to be understood that the terminology which has been used is intended to be in the nature of words of description rather than limitation.

Obviously, many modifications and variations of the present invention are possible, in light of the above teachings. It is, therefore, to be understood the invention may be practiced otherwise than as specifically described.

I claim as follows:

1. A surgical hand glove having a body shaped in the form of a hand, said body comprising
    (a) first and second layers comprising a fibrous material, and, sandwiched between said first and second layers,
    (b) a layer of a composite material which comprises
        (i) a polymeric matrix, and, embedded therein,
        (ii) whiskers selected from the group consisting of carbon whiskers, silicon carbide whiskers and mixtures thereof.

2. The surgical hand glove of claim 1 wherein said polymeric material is a latex.

3. The surgical hand glove of claim 1 wherein said fibrous material is woven KEVLAR ®.

4. The surgical hand glove of claim 1 wherein said polymeric matrix is a latex, said whiskers are carbon whiskers having a diameter ranging from about 0.00015 to 0.0005 inches and a length ranging from about 0.0625 to 0.125 inches, and said fibrous material is woven KEVLAR ®, and wherein the volumetric ratio of said whiskers to said polymeric matrix is about 28.5%.

\* \* \* \* \*